United States Patent [19]

Raspanti

[11] Patent Number: 5,346,691
[45] Date of Patent: Sep. 13, 1994

[54] S-TRIAZINE DERIVATIVES AS LIGHT STABILIZERS

[75] Inventor: Giuseppe Raspanti, Bergamo, Italy

[73] Assignee: 3V Inc., Weehawkin, N.J.

[21] Appl. No.: 63,747

[22] Filed: May 20, 1993

[51] Int. Cl.$^5$ .......... A61K 7/42; C07D 251/70
[52] U.S. Cl. .................. 424/59; 424/401; 514/245; 544/197
[58] Field of Search ............ 544/197; 424/401, 59; 514/245

[56] References Cited

U.S. PATENT DOCUMENTS 4,617,390 10/1986 Hoppe et al. .......... 544/197
4,978,523 12/1990 Motegi et al. .......... 424/59

*Primary Examiner*—Nicholas S. Rizzo
*Assistant Examiner*—Y. N. Gupta
*Attorney, Agent, or Firm*—Griffin Butler Whisenhunt & Kurtossy

[57] ABSTRACT

S-triazine derivatives of formula (I):

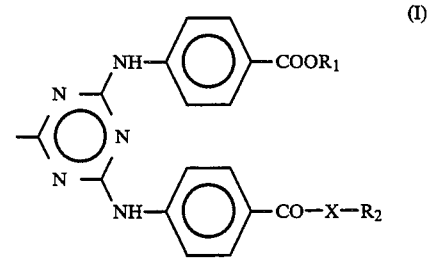

a process for the preparation thereof and the use thereof as light stabilisers.

6 Claims, No Drawings

S-TRIAZINE DERIVATIVES AS LIGHT STABILIZERS

The present invention relates to s-triazine derivatives, the process for the preparation thereof and the use thereof as light stabilisers.

The compounds of the invention have the following formula (I):

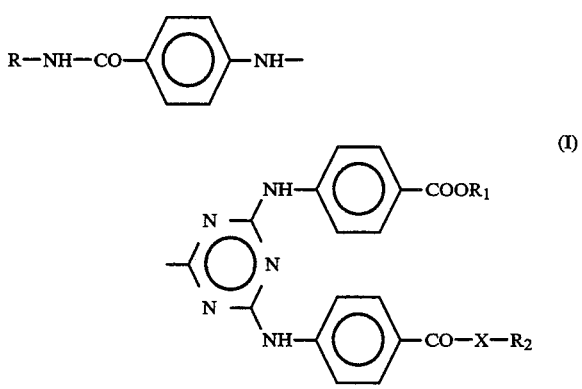

in which
R is $C_1$-$C_{18}$ straight or branched alkyl, $C_5$-$C_{12}$ cycloalkyl optionally substituted with one or more $C_1$-$C_4$ alkyl;
X is oxygen or the —NH— group;
$R_1$ has the same meanings as R or it is hydrogen, an alkali metal, an ammonium group or a group of formula (II):

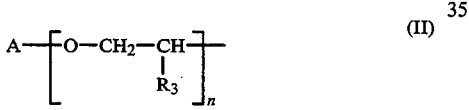

in which A is $C_1$-$C_{18}$ straight or branched alkyl, $C_5$-$C_8$ cycloalkyl, aryl optionally substituted with one or more $C_1$-$C_4$ alkyl, $R_3$ is hydrogen or methyl and n can be an integer from 1 to 10;

$R_2$ has the same meanings as R when X is the —NH— group; and it has the same meanings as $R_1$ when X is oxygen.

Examples of $C_1$-$C_{18}$ alkyl groups comprise methyl, ethyl, isopropyl, t-butyl, n-hexyl, 2-ethylbutyl, 2-ethylhexyl, 1,1,3,3-tetramethylbutyl.

Examples of $C_5$-$C_8$ or $C_5$-$C_{12}$ cycloalkyl groups optionally substituted with $C_1$-$C_4$ alkyl comprise cyclohexyl, 2-, 3- or 4-methylcyclohexyl, cyclopentyl.

Examples of aryl groups optionally substituted with $C_1$-$C_4$ alkyl comprise phenyl, 2-, 3- or 4-methylphenyl.

Preferred compounds of formula (I) are those in which X is oxygen and $R_1$ and $R_2$, which are the same, are $C_1$-$C_{18}$ straight or branched alkyl groups, $C_5$-$C_{12}$ cycloalkyl groups optionally substituted with $C_1$-$C_4$ alkyl or a group of formula (II) wherein $R_3$ is hydrogen, A is $C_1$-$C_{18}$ alkyl and n is 2.

Preferred compounds of formula (I) also are those in which X is —NH— and $R_1$ and $R_2$, which are the same or different, are $C_1$-$C_{18}$ straight or branched alkyl groups or $C_5$-$C_{12}$ cycloalkyl groups optionally substituted with $C_1$-$C_4$ alkyl groups.

Ultraviolet radiations of sunlight are known to exert a damaging action on skin tissue and to cause the degradation of polymers. By using particular compounds, the so-called sunscreens, which are capable of absorbing the UV part of solar radiation, the damaging effects and the aging of the skin and polymer materials can be prevented or, at least, slowed down.

A number of substances have been studied and tested as protecting agents, and an extensive patent literature exists on this subject, in which compounds belonging to different chemical classes are proposed, which are capable of absorbing in the ultraviolet region, particularly the radiation from 290 to 320 nm, the so-called UV-B, that is the most noxious.

Only a few of the compounds proposed up to now as sunscreens proved suitable for the practical application. Among these, p-methoxy-cinnamic acid and p-dimethylaminobenzoic acid esters, benzotriazoles and hydroxybenzophenones.

A common drawback of all the se compounds is the low power thereof to absorb the radiation from 290 to 320 nm, which makes necessary to use relatively large amounts thereof in cosmetic compositions to obtain an optimum light-protecting capability.

An optimum UV absorber should have the following characteristics:
1) high specific extinction E' at 290–320 nm, thus resulting in a low dosage and accordingly cost-savings and a minimum toxicological risk;
2) light stability;
3) heat stability;
4) oxidation stability;
5) stability at different pH;
6) good solubility in base substances commonly used for the preparation of cosmetic formulations;
7) negligible toxicity;
8) colour and odour which are compatible with the envisaged uses;
9) comparatively high molecular weight, therefore with a lower probability of absorption by the skin and a higher safety from the toxicological point of view;
10) compatibility with the various substances generally used in dermatological formulations.

In DE 3 206 398 Patent which is an equivalent of U.S. Pat. No. 4,617,390, s-triazine derivatives are disclosed, obtained by reacting trichlorotriazine with p-aminobenzoic acid esters, which derivatives highly absorb at the UV-B region. However, these compounds are very poorly soluble in the solvents commonly used in the formulation of sun creams, thus making them very difficult to use, particularly when an increased percentage of the light-protecting agent is needed to prepare formulations having a high sun protection factor.

The sun protection factor (SPF) is a unit of measurement of the light-protecting power of a sun screen or of a cosmetic formulation containing one or more sunscreens. It is directly related to the specific extinction and accordingly to the light-protecting agent present in the cosmetic formulation.

Now it has been found that the compounds according to present invention, besides absorbing very highly in the UV-B region and having a very high SPF, surprisingly show an excellent solubility in the solvents commonly used as components in the sunscreens formulations.

Therefore, a further object of the invention resides in the use of the compounds of formula (I) as sunscreens and light stabilisers, thanks to the capability thereof of exerting a surprising protecting activity on the skin from the noxious components of sunlight radiation.

The compounds of the invention are also valuable for use in light stabilization of synthetic polymers, in order to prevent light degradations and alterations.

Compounds (I), besides having a very high absorption in the UV-B region as well as an excellent solubility, have other characteristics necessary for the application in practice, such as heat stability, no toxicity and the like.

The compounds of the present invention can be prepared by reacting triazine derivatives of formula (III)

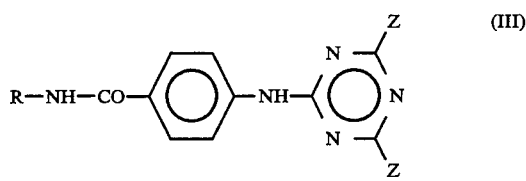

with p-aminobenzoic acid esters of formula (IV)

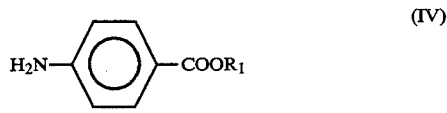

or by reacting triazine derivatives of formula (V)

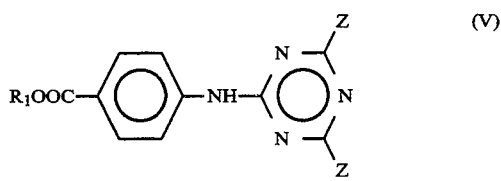

with p-aminobenzoic acid amides of formula (VI)

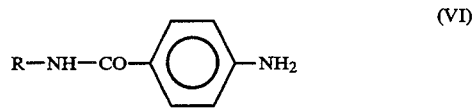

In formulae (III)–(VI), Z is bromine or preferably chlorine whereas R and $R_1$ have the meanings described above.

The compounds of formulae (III)–(VI) are known or they can be prepared according to known methods. The reaction is carried out at a temperature from 50° to 200° C. in a suitable solvent.

Suitable solvents in which the reaction is carried out are, for example, acetonitrile; ketones, such as acetone, methyl ethyl ketone; ethers such as diethyl ether, diisopropyl ether, tetrahydrofuran, dioxane; aliphatic or aromatic hydrocarbons such as pentane, heptane, cyclohexane, benzene, toluene, xylene or mixtures thereof; aliphatic carboxylic acid esters such as ethyl acetate.

The reaction can be effected either in the absence or in the presence of acid acceptors, such as alkali or alkaline-earth metal hydroxides, alkali metal bicarbonates or carbonates, in molar ratios of 2–3 moles of compounds of formula (IV) or (VI) to mole of compounds of formula (III) or (V).

The intermediates of formula (III) and (V), before the subsequent reaction with the compounds of formula (IV) and (VI), can be recovered and purified or, more easily, they are reacted as crude products, considering them as first step of a multi-step synthesis.

The reactions of trihalotriazines to replace the three halogen atoms with amino residues, which can be the same or different, are known and widely described in technical literature, particularly in the literature concerning some kinds of dyes and optical bleachers.

According to one of the preferred embodiments of the invention, the compositions containing the compounds of formula (I) are used to protect the skin from the damaging effects of sunlight radiations.

The compounds according to the present invention can be added, of course also in combination with other stabilizers, to the cosmetic formulations as well as to synthetic polymers, generally in amounts ranging from 0.05 to 15%, preferably from 0.1 to 10% by weight of the polymer or cosmetic formulation.

The cosmetic formulations can be of various kinds and they can be used for different purposes. Generally they are in form of ointments, creams, lotions, emulsions.

The compounds of formula (I) are added either to protect the formulations themselves, for example to prevent undesired discolourations, or to protect the skin treated with the formulation from the damaging action of UV-B radiations, which causes erythema and accelerates the aging of the skin making it prematurely dry, wrinkled or squamous.

The following examples illustrate the invention.

EXAMPLE 1

A mixture of 167 g of p-nitrobenzoic acid, 204 g of 2-ethyl-1-butanol and 3.5 g of p-toluenesulfonic acid is refluxed and stirred for 2 hours, separating the formed water. After that, the alcohol excess is distilled off, then the formed product is distilled at 150° C. and 0.04 mmHg, to obtain 209 g of 2-ethylbutyl p-nitrobenzoate in form of a light yellow viscous liquid.

EXAMPLES 2-8

Following the procedure described in Example 1, recovering and purifying the products by distillation or crystallization, the esters listed in Table 1 are prepared.

TABLE 1

$O_2N-\langle O \rangle-COOR_1$

| Example | $R_1$ | M.P. °C. or E.P. |
|---|---|---|
| 2 | $(CH_3)_2CH-CH_2-$ | 66–68 |
| 3 | $CH_3(O-CH_2-CH_2)_2-$ | not det. |
| 4 | $CH_3-$ | not det. |
| 5 | ![CH3, CH3, CH3 trimethylcyclohexyl] | 78–80 |
| 6 | $C_{14}H_{29}-$ | 50–52 |
| 7 | $C_4H_9-CH(C_2H_5)-CH_2$ | not det. |

TABLE 1-continued

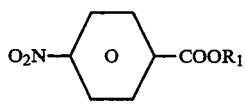

| Example | R₁ | M.P. °C. or E.P. |
|---|---|---|
| 8 | <img CH₃ cyclohexyl> | 158–160/0.5 mbar |

EXAMPLE 9

32.5 g of isopropylamine dissolved in 250 ml of acetone are added with 71 g of a 30% sodium hydroxide aqueous solution. This mixture, cooled to 0° C., is slowly added with 92.7 g of p-nitrobenzoyl chloride dissolved in 300 ml of acetone, cooling with an ice bath to keep temperature from 0° to 5° C. Subsequently stirring is continued for 1 more hour allowing temperature to raise to 20°–30° C. Then the reaction mixture is poured into cold water. The formed precipitate is filtered, washed with water, dried and crystallized from isopropanol. 77 g of N-isopropyl-p-nitrobenzamide are obtained as a whitish solid substance with m.p. 152°–154° C.

EXAMPLES 10–15

Following the procedure of Example 9, the p-nitrobenzamides listed in Table 2 are obtained.

TABLE 2

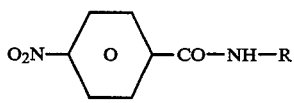

| Example | R | M.P. (°C.) |
|---|---|---|
| 10 | (CH₃)₃C— | 159–161 |
| 11 | CH₃— | 212–214 |
| 12 | n-C₆H₁₃— | 86–88 |
| 13 | C₄H₉—CH(C₂H₅)—CH₂— | not det. |
| 14 | (CH₃)₃C—CH₂—C(CH₃)₂— | 114–116 |
| 15 | cyclohexyl | 202–204 |

EXAMPLE 16

200 g of 1-ethylbutyl p-nitrobenzoate of Example 1, 900 ml of methanol, 12 g of acetic acid and 16 g of 50% Raney Nickel in water are placed into an autoclave. The autoclave is washed with nitrogen, then with hydrogen. After that, the nitro derivative is reduced at a temperature of 75° C. and under a pressure of 30 bar. The catalyst is filtered off, then the mixture is evaporated to dryness and the residual product is crystallized with hexane.

132 g of 2-ethylbutyl p-aminobenzoate are obtained, as a whitish substance with m.p. 52°–53° C.

EXAMPLES 17–29

Following the procedure of Example 16, by hydrogenating the compounds of Examples 2–15, the compounds listed in Table 3 are obtained.

TABLE 3

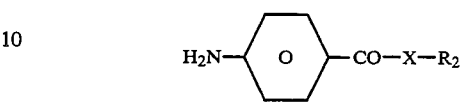

| Example | R | X | M.P. (°C.) or E.P. |
|---|---|---|---|
| 17 | (CH₃)CH— | NH | 151–153° C. |
| 18 | CH₃— | O | 109–111 |
| 19 | (CH₃)₂CH—CH₂— | O | 57–59 |
| 20 | (CH₃)₃C— | NH | 124–126 |
| 21 | CH₃— | NH | 177–179 |
| 22 | CH₃—(O—CH₂—CH₂)₂— | O | 204–206/1 mbar |
| 23 | n-C₆H₁₃— | NH | 107–109 |
| 24 | C₄H₉—CH(C₂H₅)—CH₂— | O | 49–51 |
| 25 | C₄H₉—CH(C₂H₅)—CH₂— | NH | 110–112 |
| 26 | trimethylcyclohexyl (CH₃, CH₃, CH₃) | O | 62–63 |
| 27 | cyclohexyl | NH | 181–183 |
| 28 | C₁₄H₂₉— | O | 63–65 |
| 29 | CH₃-cyclohexyl | O | 188–190/0.5 mbar |

EXAMPLE 30

A solution of 37 g of trichlorotriazine in 450 ml of acetone, cooled to 0° C., is added with 17.6 g of sodium bicarbonate, then slowly with 39 g of tert-butyl p-aminobenzamide (compound of Example 20), keeping temperature at 0° C. by cooling. Subsequently the mixture is stirred for 30 minutes, then 150 ml of water are added and stirring is continued for ½ hour; then the precipitate is filtered, washed many times with water and dried under vacuum.

64 g of dichlorotriazine derivative are obtained as a white substance with m.p. >250° C.

EXAMPLES 31–39

Following the procedure in Example 30, starting from trichlorotriazine and compounds of Examples 16–29, the dichlorotriazine derivatives listed in Table 4 are prepared.

TABLE 4

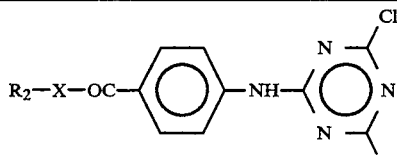

| Example | R | R₁ | R₂ | | M.P. (°C.) |
|---|---|---|---|---|---|
| 41 | CH₃— | CH₃, CH₃—, CH₃ (cyclohexyl with 3 methyl groups) | CH₃, CH₃—, CH₃ (cyclohexyl with 3 methyl groups) | O | 175-178 |
| 42 | CH₃— | C₄H₉—CH(C₂H₅)CH₂— | C₄H₉CH(C₂H₅)—CH₂— | O | 108-110 |
| 43 | (CH₃)₃C— | CH₃ (methylcyclohexyl) | CH₃ (methylcyclohexyl) | O | 149-152 |
| 44 | (CH₃)₃C— | C₄H₉—CH(C₂H₅)—CH₂— | C₄H₉CH(C₂H₅)CH₂+ | O | 91-93 |
| 45 | (cyclohexyl) | C₂H₅—CH(C₂H₅)—CH₂— | C₂H₅—CH(C₂H₅)—CH₂— | O | 148-151 |
| 46 | n-C₆H₁₃— | CH₃ (methylcyclohexyl) | CH₃ (methylcyclohexyl) | O | 129-132 |
| 47 | C₄H₉—CH(C₂H₅)—CH₂— | CH₃— | C₄H₉CH(C₂H₅)—CH₂— | NH | 231-233 |
| 48 | C₄H₉—CH(C₂H₅)—CH₂ | C₄H₉—CH(C₂H₅)—CH₂— | C₄H₉CH(C₂H₅)—CH₂— | O | 91-93 |
| 49 | (CH₃)₃C—CH₂—O(CH₃)₂— | (CH₃)₂—CH—CH₂— | (CH₃)₂—CH—CH₂— | O | 152-154 |
| 50 | C₄H₉CH(C₂H₅)—CH₂— | C₄H₉—CH(C₂H₅)—CH₂ | C₄H₉—CH(C₂H₅)—CH₂ | NH | 104-106 |
| 51 | (CH₃)₃C—CH₂—C(CH₃)₂— | CH₃(—O—CH₂CH₂)₂— | CH₃(—O—CH₂—CH₂)₂— | O | 69-71 |
| 52 | (CH₃)₂CH— | C₁₄H₂₉ | (CH₃)₂—CH— | NH | 109-112 |
| 53 | (CH₃)₂—CH— | C₄H₉—CH(C₂H₅)—CH₂— | C₄H₉—CH(C₂H₅)—CH₂— | O | 110-112 |

| Example | R₂ | X | M.P. (°C.) |
|---|---|---|---|
| 31 | CH₃— | NH | 22 260 |
| 32 | CH₃— | O | >260 |
| 33 | (CH₃)₂CH— | NH | >260 |
| 34 | C₄H₉—CH(C₂H₅)—CH₂— | O | 245-248 |
| 35 | C₄H₉—CH(C₂H₅)—CH₂— | NH | 250-252 |
| 36 | (CH₃)₃C—CH₂—C(CH₃)₂— | NH | 240-243 |
| 37 | nC₆H₁₃— | NH | 220-223 |
| 38 | C₁₄H₂₉— | O | 205-207 |
| 39 | (cyclohexyl) | NH | >260 |

EXAMPLE 40

17 g of the compound of Example 30 and 26 g 2-ethylhexyl p-aminobenzoate (Example 24) in 250 ml of xylene are stirred under reflux for 4 hours. Then xylene is distilled off and the residue is recrystallized from a toluene and hexane mixture.

35 g of compound of formula (I) are obtained (R=(CH₃)₃C—, R₁=R₂=C₄H₉—CH(C₂H₅)—CH₂—; X=O) as a white substance with m.p. 101°-103° C.

EXAMPLES 41-53

Following the procedure of Example 40, reacting the triazine derivatives of Table 4 with the compounds of Table 3, the compounds of formula (I) listed in Table 5 are prepared.

TABLE 5 (above)

In the following Table 6, the solubilities in isopropyl myristate (which is the solvent generally used for the preparation of sun creams) and the specific extinctions of the compounds of formula (I) are compared with those of the product of DE 3 205 398 patent (compound C), which is commercially available.

TABLE 6

| Example | max (nm) | E' | Solubility in isopropyl myristate at 20° C. g/100 ml |
|---|---|---|---|
| 42 | 311 | 1647 | >20 |
| 43 | 311 | 1624 | >20 |
| 45 | 310 | 1613 | >20 |
| 46 | 311 | 1558 | >20 |
| 49 | 311 | 1689 | >20 |
| 50 | 310 | 1449 | >20 |
| 53 | 310 | 1607 | >20 |
| Compound C | 313 | 1563 | >5 |

EXAMPLE 54

Preparation of a sun cream

Mixture A

A mixture of 44 g of water, 0.5 g of the thickening agent Synthalen L (cross-linked polyacrylic acid), 5 g of glycerin, 0,3 g of imidazolidinylurea and 0.15 g of methyl p-hydroxybenzoate is prepared.

Mixture B 5 g of the compound of Example 43 are dissolved in 25 g of isopropyl myristate, the solution is added with 5 g of vaseline oil, 2 g of cetyl alcohol, 5 g of glycerin monostearate, 5 g of capric/caprylic triglyceride, 2 g of polysorbate 20, 0,2 g of bee wax and 0.05 g of propyl p-hydroxybenzoate.

The mixtures A and B are heated separately to 70° C., then mixture B is added to mixture A with stirring. The resulting emulsion is neutralized adding 0.75 g of triethanolamine and finally 0.02 g of perfume are added at a temperature below 35° C.

I claim:

1. Compounds of formula (I):

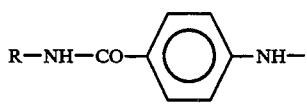

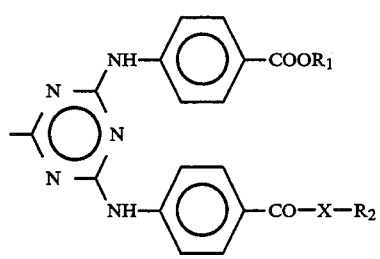

(I)

in which

R is $C_1$-$C_{18}$ straight or branched alkyl, $C_5$-$C_{12}$ cycloalkyl optionally substituted with one or more $C_1$-$C_4$ alkyl;

X is oxygen or the —NH— group;

$R_1$ has the same meanings as R or it is hydrogen, an alkali metal, an ammonium group or a group of formula (II):

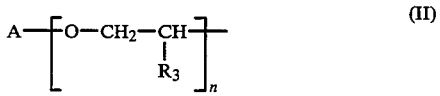

in which A is $C_1$-$C_{18}$ straight or branched alkyl, $C_5$-$C_8$ cycloalkyl, aryl optionally substituted with one or more $C_1$-$C_4$ alkyl, $R_3$ is hydrogen or methyl and n can be an integer from 1 to 10;

$R_2$ has the same meanings as R when X is the —NH— group; and it has the same meanings as $R_1$ when X is oxygen.

2. Compounds according to claim 1 in which X is oxygen and $R_1$ and $R_2$, which are the same, are $C_1$-$C_{18}$ straight or branched alkyl groups, $C_5$-$C_{12}$ cycloalkyl groups optionally substituted with $C_1$-$C_4$ alkyl or a group of formula (II) wherein $R_3$ is hydrogen, A is $C_1$-$C_{18}$ alkyl and n is 2.

3. Compounds according to claim 1 in which X is —NH— and $R_1$ and $R_2$, which are the same or different, are $C_1$-$C_{18}$ straight or branched alkyl groups or $C_5$-$C_{12}$ cycloalkyl groups optionally substituted with $C_1$-$C_4$ alkyl groups.

4. Dermatological and cosmetic compositions comprising a sunlight radiation protecting effective amount of at least one of the compounds of claim 1 and a topical carrier therefor.

5. Cosmetic and dermatological compositions according to claim 4 containing from 0.05 to 10% by weight of the compounds of claim 1.

6. A method for protecting skin from sunlight radiations comprising applying to the skin a composition according to claim 5.

* * * * *